United States Patent [19]

Plowman et al.

[11] 4,251,211
[45] Feb. 17, 1981

[54] FLUID CONTROL SYSTEM FOR DENTAL CONSOLE

[75] Inventors: Richard E. Plowman, York; Bruce J. Spencer, Spring Grove, both of Pa.

[73] Assignee: Dentsply Research & Development Corp., Milford, Del.

[21] Appl. No.: 95,009

[22] Filed: Nov. 16, 1979

[51] Int. Cl.³ .............................................. A61C 1/02
[52] U.S. Cl. ...................... 433/98; 433/77; 433/101
[58] Field of Search ............. 137/376, 98; 433/27, 433/28, 77, 103, 108, 98

[56] References Cited

U.S. PATENT DOCUMENTS

| | | | |
|---|---|---|---|
| 3,638,310 | 2/1972 | Austin | 433/98 |
| 3,875,958 | 4/1975 | Miller | 433/98 |
| 3,904,841 | 9/1975 | Swatman | 433/98 |
| 3,918,161 | 11/1975 | Morgan | 433/98 |
| 3,961,640 | 6/1976 | Baker | 433/98 |
| 4,145,813 | 3/1979 | Hall | 433/98 |

Primary Examiner—Robert Peshock
Attorney, Agent, or Firm—C. Hercus Just

[57] ABSTRACT

This invention pertains to a dental operatory console system including one or more fluid control valves for driving air and water to be delivered to dental handpieces supported for ready removal from a pivoted holder to provide adjustable angular positioning of the handpiece, one of such pivoted holders being adjacent each control valve and including a lockout for the valve plunger when the handpiece is removed from the holder, such as when changing burs, to prevent accidental operation of the air and water valve for delivery to the handpiece. The pivoted holder is readily removable for servicing the valve and the fluid circuit for water and air between a source of the same and a plurality of handpieces in the console includes shuttle valves to permit the use of a single air pressure gage for the system rather than a gage for each handpiece as in conventional multiple-handpiece consoles.

17 Claims, 10 Drawing Figures

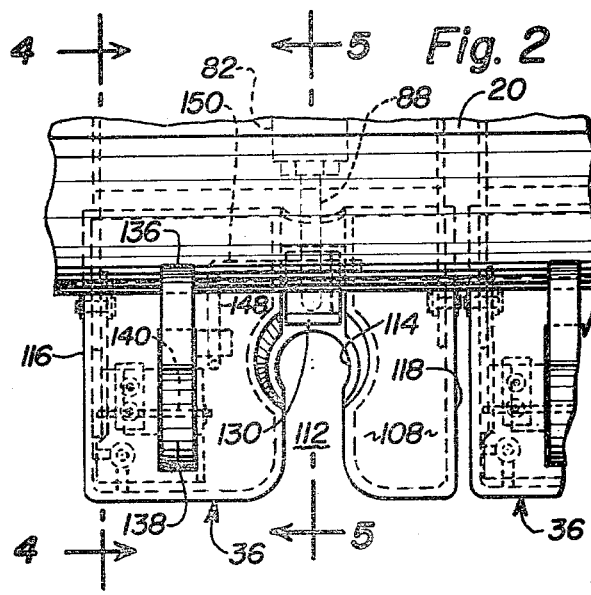
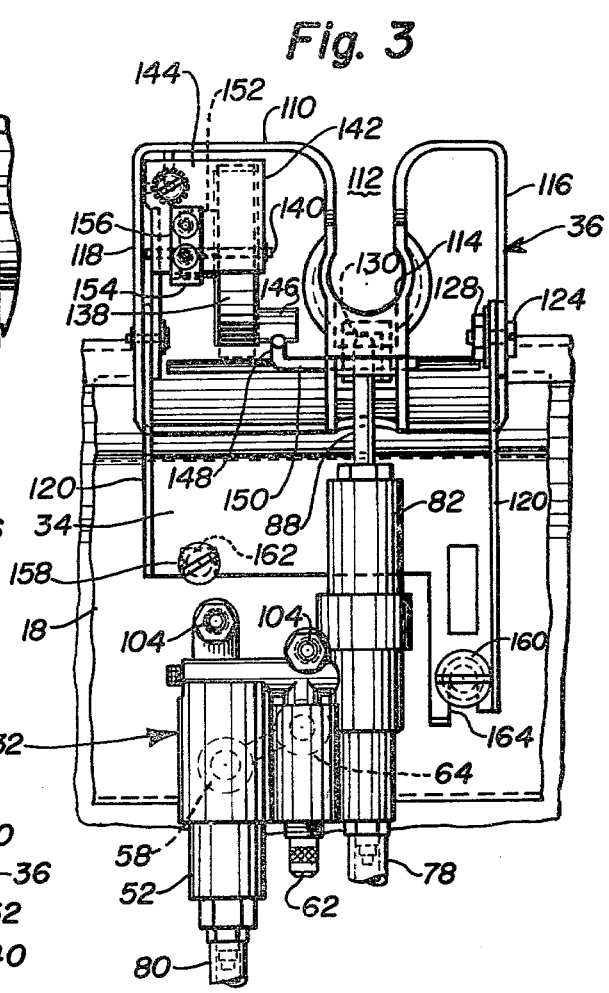
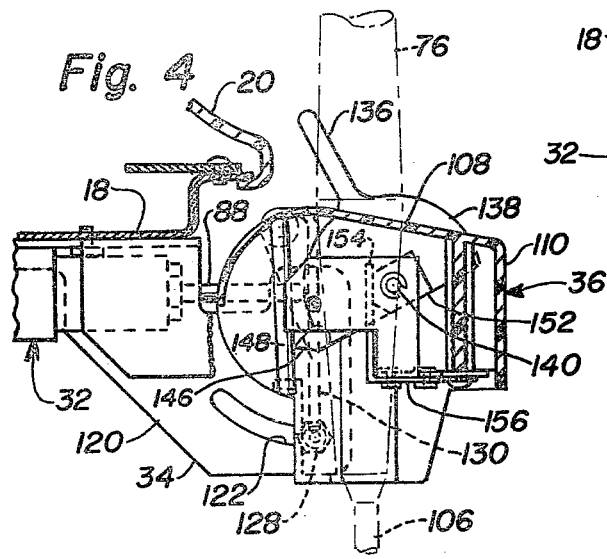
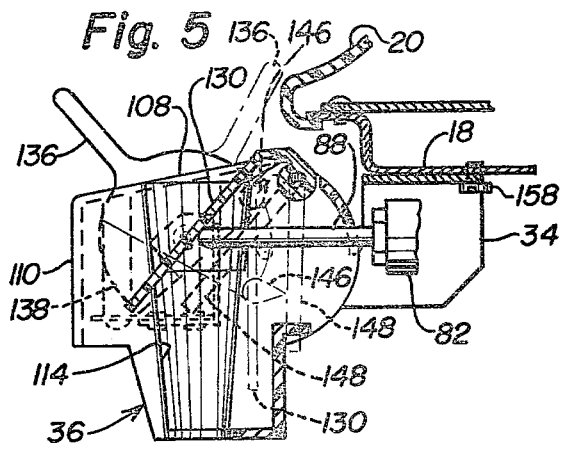
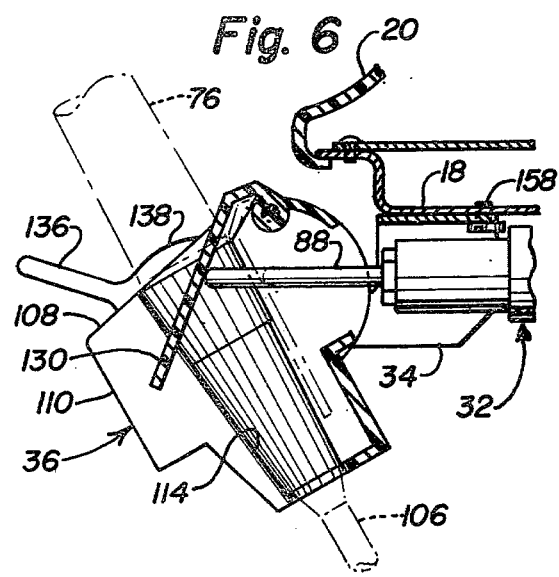

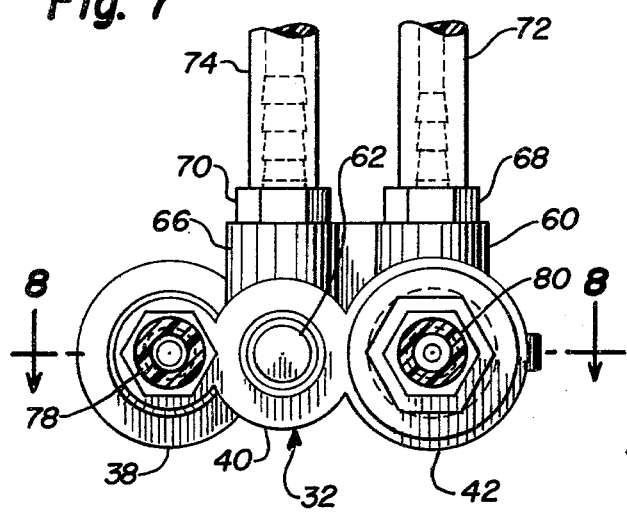
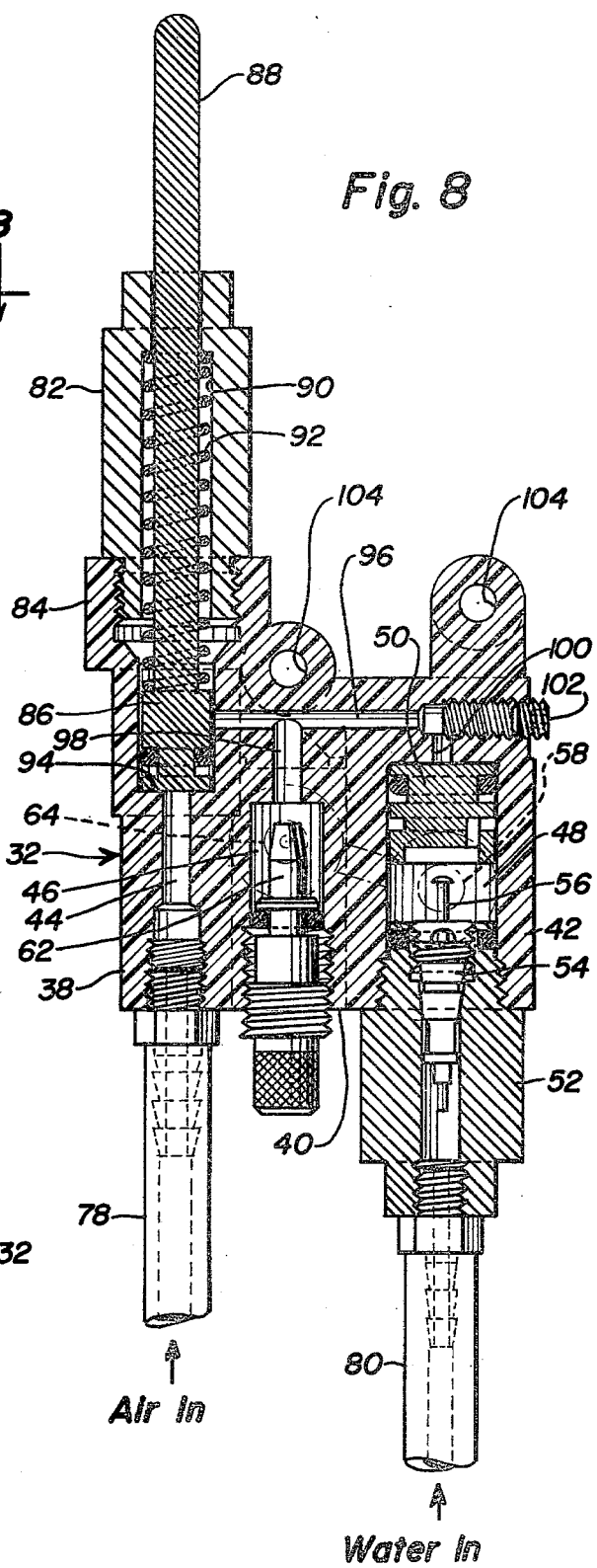
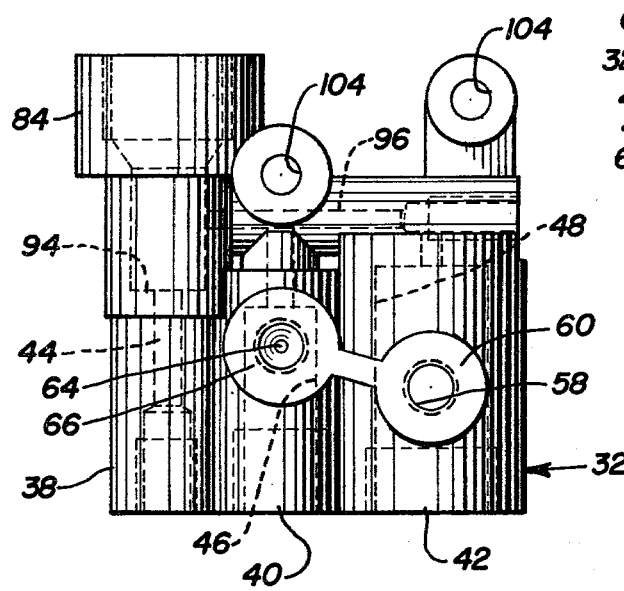

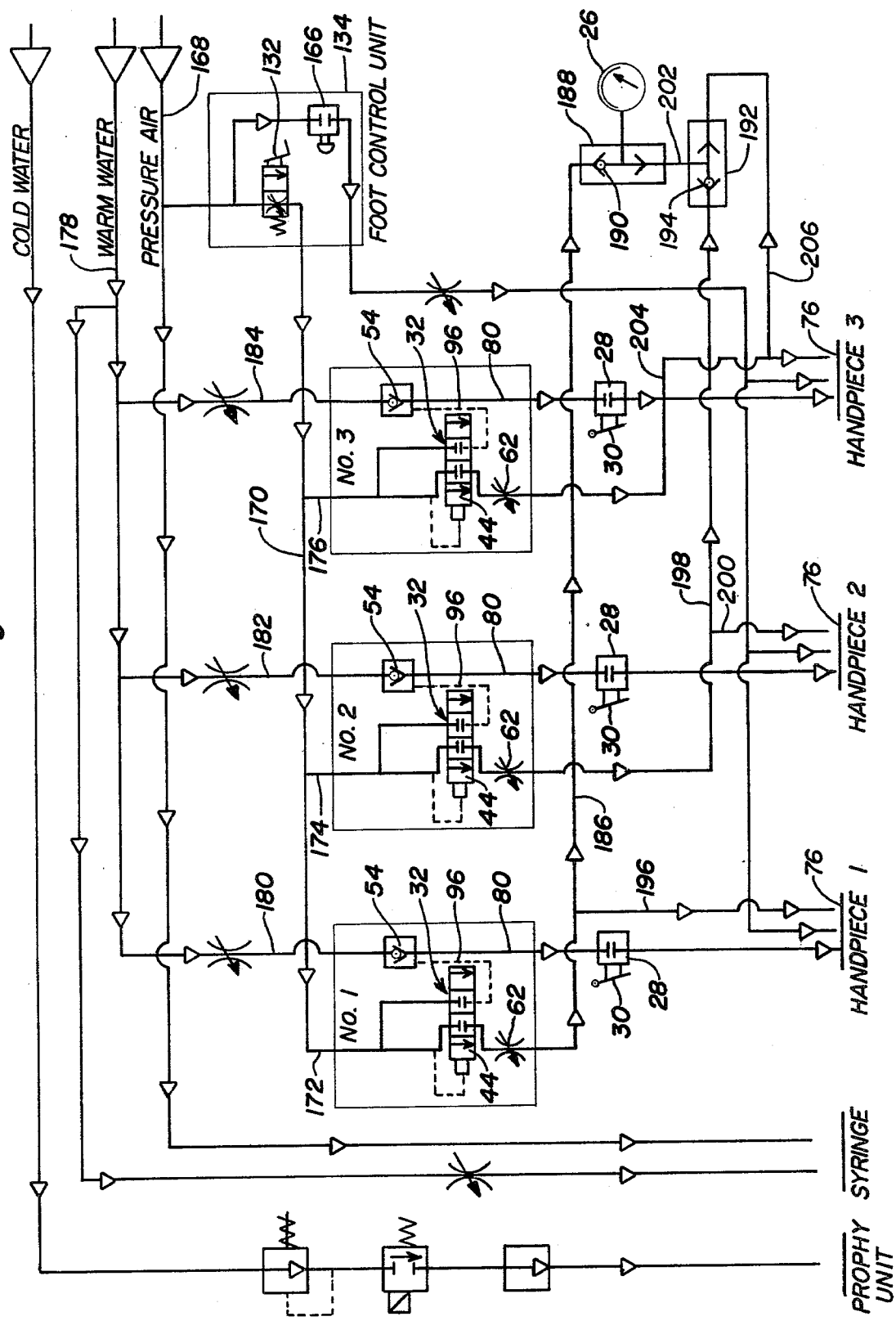

FLUID CONTROL SYSTEM FOR DENTAL CONSOLE

BACKGROUND OF THE INVENTION

This invention pertains to a particular type of valve employed in a dental console for delivering air under pressure to drive dental handpieces and also to furnish water thereto, when desired, in a manner which is less complex and more effective than is possible with known devices of similar type. The employment of said valve has necessitated the development of improved, adjustable supports for dental handpieces mounted adjacent said valve and including certain facilities to permit ready servicing of the valve when required and also including lockout mechanism to prevent actuation of the valve when a dental handpiece is removed from the support for purposes other than the normal function thereof, and an improved air and water distribution system is provided which is capable of servicing a plurality of dental handpieces, yet employ only a single air pressure gage for each console in which the plurality of handpieces are mounted.

The type of valve to which the present invention is directed essentially is a refinement of the air and water control valve comprising the subject matter of U.S. Patent Application Ser. No. 944,223, in the name of Neri, filed Sept. 20, 1978, particularly for purposes of simplifying the manufacturing, as well as mounting thereof, in a dental console, the assignee of the present invention being licensed under the above-identified patent application. As will be seen from said application, the foot control for operating dental handpieces which are serviced by the valve comprising the subject matter of the application requires two foot treadles, one being for purposes of actuating the air control valve and the other operating another air control valve which, in turn, actuates means to open a water supply to a handpiece. One objective of the present invention is to obviate the need for two treadles in the foot control and employ only a single one.

In general, it has been quite common to employ two treadles in a foot control respectively for purposes of effecting the delivery of air and water to a dental handpiece, as in the Neri invention referred to above. One such prior device is exemplified in U.S. Pat. No. 3,067,765 in the name of Aymar, dated Dec. 11, 1962. However, the use of a single pedal or button in a foot control, solely for purposes of controlling the supply of air to a handpiece, is old and two typical examples thereof are found in U.S. Pat. No. 3,242,572 in the name of Staunt, dated Mar. 29, 1966 and U.S. Pat. No. 3,855,704, in the name of Booth, dated Dec. 24, 1974.

It also is known to employ lockout devices in dental consoles associated with the air valves for purposes of preventing the flow of air to a handpiece when it is desired to remove a handpiece from the holder therefore in a console, such as for purposes of removing or replacing a bur in the handpiece. Typical examples of such prior lockout devices are found in U.S. Pat. No. 3,672,059 in the name of Booth, dated June 27, 1972; U.S. Pat. No. 3,904,841 in the name of Swatman, dated Sept. 9, 1975; and U.S. Pat. No. 3,918,161 in the name of Morgan et al, dated Nov. 11, 1975. However, the lockout structure of the present invention has been designed specifically for use with the support for the dental handpiece in said invention and has required the development of details compatible therewith.

It also is known to employ a single pressure gage in a dental console in which a plurality of handpieces are employed for purposes of indicating the pressure of the air present in the air-distribution system to said handpieces. One example of such an arrangement comprises the subject matter of U.S. Pat. No. 3,461, 561 in the name of Valeska et al, dated Aug. 19, 1969, but the means by which the single pressure gage is made feasible in the present invention requires a different type of circuitry than that employed in said prior U.S. Patent.

SUMMARY OF THE INVENTION

As alluded to in a general nature hereinabove, the present invention essentially centers around a particular type of control valve for supplying operating air and, when water is desired, also supplying water to a dental handpiece, said valve being capable of manufacture from suitable plastics or synthetic resin to provide a very compact valve body in which a plurality of side-by-side elongated cylindrical ports are formed, all of which extend inward from one end of the body, two of said ports respectively accommodating inlet means for air and water and another of said ports accommodating a needle valve which controls the supply of driving air to a dental handpiece, the outer ends of said ports also being molded with threads in situ respectively to accommodate fittings by which conduits may be attached for delivering air and water respectively to said body of the valve and the interior of said body having a transverse air passage commonly communicating with the inner ends of all of said ports.

Another object of the invention ancillary to the foregoing object is to provide in alignment with the air inlet port but extending oppositely therefrom, a valve spool which includes a control rod projecting suitably from said opposite end of the valve body and operable to control the flow of air from the air inlet port respectively to the other ports in the valve body, said spool being retained in closed position by an internal spring associated with the control rod.

Another object of the invention is to provide in association with the water inlet port, a movable member in line with said port, and also provide a valve actuating piston within said port that is engageable with said movable valve member when air from the transverse fluid passage within the body of the valve operates said piston to engage said valve member and thereby open said port for the flow of water through an intermediate discharge port extending transversely from said water inlet port and in communication with the interior of said water inlet port when said valve member has been moved to open position.

Still another object of the invention is to provide an adjustable support for a dental handpiece mounted within a console immediately adjacent said aforementioned valve, said support being connected pivotally to a bracket to permit said support to be pivotally moved through a limited arc to support a dental handpiece between a substantially vertical and in outwardly inclined positions for selective engagement of the handpiece by an operator, such as a dentist or dental assistant.

One further object of the invention is to provide a lockout mechanism associated with the support for the handpiece and engageable with the control rod of the valve spool associated with the air inlet port and comprising a small pivoted lever movable between operative and inoperative lockout positions for purposes of engaging said spool to hold the same in closed position within the air inlet port when a dental handpiece is removed from the support, such as for purposes of exchanging burs and any other desired operations which require the handpiece being removed from the support.

In view of the fact that it is preferred that the support for the handpiece be mounted immediately adjacent and forwardly of the control valve of the type referred to above, it is another object of the invention to connect the bracket for the handpiece support in a readily detachable manner to the forward portion of a transverse frame member in a dental console in which the aforementioned elements are mounted and thereby permit ready access to the valve per se, such as for servicing or otherwise.

By employing a single air pressure gage, for economy, in a dental console in which a plurality of dental handpieces are accommodated, it is still another object of the invention to provide air and water conduit circuits in which a plurality of shuttle valves are included in a manner to insure that air pressure in the system will be registered by the single air pressure gage regardless of which dental handpiece is being employed at any particular time.

Details of the foregoing objects and of the invention, as well as other objects thereof, are set forth in the following specification and illustrated in the accompanying drawings comprising a part thereof.

BRIEF DESCRIPTION OF THE DRAWINGS

FIG. 2 is a fragmentary plan view of the support for a handpiece adjacent the lower edge of the upstanding front panel of the console, as seen on the line 2—2 of FIG. 1.

FIG. 3 is a bottom plan view looking upward from FIG. 1 as seen on the line 3—3 thereof and illustrating fragmentarily a portion of the console to which is attached a bracket for the handpiece support and the control valve embodying the principles of the present invention.

FIG. 4 is a fragmentary vertical elevation of a handpiece support illustrated in FIGS. 2 and 3, as seen on the line 4—4 of FIG. 2.

FIG. 5 is a fragmentary vertical elevation of another portion of the handpiece support shown in FIG. 2, as seen on the line 5—5 thereof, a lockout member being shown in full lines in one position and in phantom in a second position in said figure.

FIG. 6 is a fragmentary vertical elevation similar to FIG. 5 but showing the handpiece support at an inclined position as distinguished from the vertical position thereof shown in FIG. 5, a fragmentary portion of the handpiece being illustrated in phantom in FIG. 6.

FIG. 7 is an end view of the valve unit embodying the principles of the present invention and illustrating fragmentarily exemplary air and water supply conduit tubes connected thereto.

FIG. 8 is a transverse sectional view of the valve unit shown in FIG. 7, as seen on the line 8—8 thereof and illustrating fragmentarily portions of air and water supply conduit tubes extending from the valve body.

FIG. 9 is a top plan view of the valve shown in FIG. 7.

FIG. 10 is an exemplary circuit diagram of air and water supply conduits and also including a plurality of diagrammatically illustrated control units for a similar plurality of handpieces, together with toggle valves for controlling the supply of water to handpieces, as desired, as well as a single pressure gage and a plurality of shuttle valves.

DETAILED DESCRIPTION OF THE PREFERRED EMBODIMENTS

Figure 1:
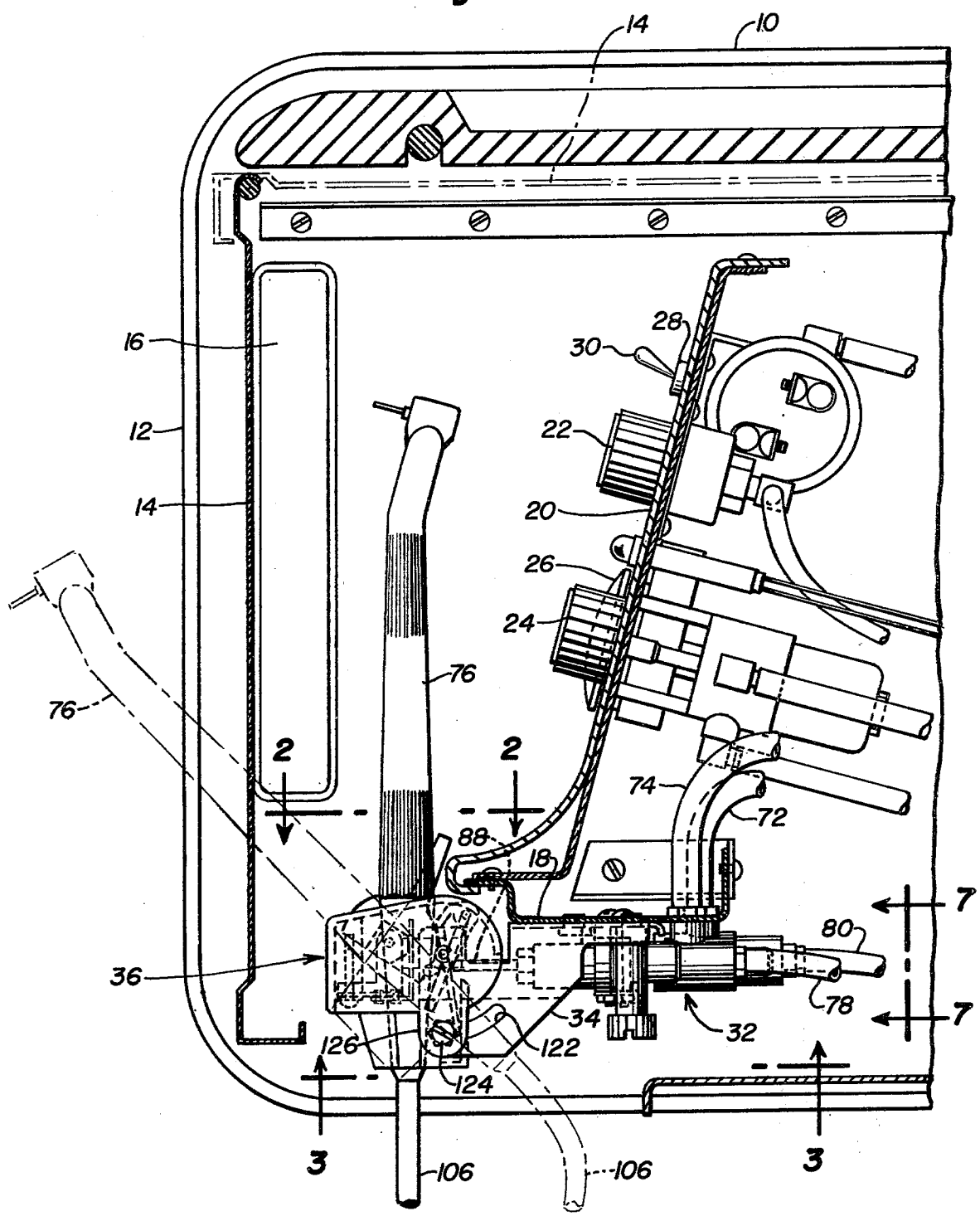
FIG. 1 is a fragmentary vertical elevation of an exemplary dental console in which an upstanding front panel is shown for supporting various control knobs, switches, and the like, as well as showing an exemplary handpiece in full line in one position with respect to a support carried by said console and, in phantom, a second slanting position of the handpiece shown, the support also being illustrated in association with a control valve embodying the principles of the present invention.

It is to be understood that the fluid control system comprising the present invention is especially designed for use in a dental console in which a plurality of different handpieces of various types and uses are mounted upon appropriate holders, usually disposed in the upper forward portion of the cabinet or housing of the console. For purposes of simplifying the drawings of this application, only a fragmentary portion of a dental console is illustrated in FIG. 1, but such illustration is suitable to illustrate the principles of the invention with the understanding that a plurality of holders is contained in said console as illustrated diagrammatically in FIG. 10, which primarily illustrates the air and water conduit circuitry of the invention, together with appropriate control valves of various types.

Referring to FIG. 1, there is illustrated fragmentarily the upper forward portion of a typical dental console to which the present invention pertains, said view comprising a vertical sectional view thereof and illustrating a shell 10 of a dental console cabinet which has an open front 12, at least in the upper portion thereof that can be closed by a movable cover 14, said cover being illustrated in the upper portion of said figure in phantom, in the stored position thereof when the front of the cabinet is to be opened. Also, to facilitate moving the cabinet, opposite sides of the cabinet are provided with elongated openings 16, which receive the fingers of an operator to facilitate moving the cabinet from a position to another. Extending between opposite sides of the cabinet there also is a sheet metal frame member 18 which extends between said opposite sides and is supported thereby, said member having a horizontal flat portion for purposes to be described.

The cabinet 10 also supports an upstanding front panel 20 upon which various manually-operable control knobs 22 and 24 are movably supported for the control of certain dental instruments included in the console, together with a pressure gage 26 included in the air conduit circuitry, which also is described hereinafter. Said panel also supports a toggle valve 28 for the water conduit circuitry, likewise described in detail hereinafter, and including a manually-operable handle 30.

One of the functions of the frame member 18 is to support a compound valve unit 32, as well as a bracket 34, upon which a dental handpiece support 36 is adjustably mounted, both of said items being described in detail hereinbelow.

COMPOUND VALVE UNIT

The compound valve unit 32 preferably is formed by injection molding from appropriate synthetic resin or plastics of a rigid nature, one highly suitable variety being sold under the trade name DELRIN 8010, said material not only having a high degree of shape retention but also possessing substantial self-lubricating properties to facilitate the movement of various movable members, such as valve members therein, described in detail below. The compound valve body of the valve unit 32 is provided with a plurality of elongated, cylindrical configurations 38, 40 and 42, which are in close side-by-side relationship, as clearly shown in FIGS. 7 and 9, the interiors of which have an elongated cylindrical port 44 which comprises water inlet means; port 46 which contains a needle valve; and port 48 which comprises a water inlet port and contains a slidable piston 50 in one end of the chamber comprising said port, the opposite end thereof threadably receiving a valve retaining nut 52 within which a water flow control valve 54 is mounted, said valve having an acuating member 56 disposed within the cavity of said bore, said cavity also having a water discharge port 58 communicating therewith, as shown in phantom in FIG. 8, and also being illustrated in FIG. 9. Water discharge port 58 is actually formed in a boss 60, which is integrally molded with the configuration 42 of the compound valve unit 32.

The elongated cylindrical port 46, which contains a needle valve 62 also is provided with an air discharge port 64 shown in phantom in FIG. 8 and also shown in FIG. 9 as being formed within another boss 66, which is integrally molded with configuration 40, within which the needle valve 62 is threadably mounted, as best shown in FIG. 8. The bosses 60 and 66 respectively are provided with fittings 68 and 70, which are threaded into preferably premolded threads within the bosses for the attachment respectively of water discharge conduit 72 and air discharge conduit 74 to be connected thereto, for delivery to a dental handpiece 76, one typical example of which is shown in FIG. 1.

Air under pressure and water respectively are delivered to the compound valve unit 32 by conduits 78 and 80 which respectively are attached at one end to suitable fittings threaded respectively into cylindrical air port 44 and cylindrical water port 48, the latter being connected to the valve retaining nut 52. Mounted in axial alignment with, but extending oppositely from, the end of the valve body configuration 38 to which the air inlet conduit 78 is connected, is a valve guide nut 82 which is threaded into a preferably premolded threaded socket 84 of the valve body 32 for purposes of slidably supporting a valve spool 86 positioned within a diametrically enlarged portion of the cylindrical air port 44 in the valve body 32, the valve spool having an elongated control rod 88 projecting from one end thereof, outwardly through and beyond the outer end of the nut 82, as clearly shown in FIG. 8, the projecting end of the control rod being for purposes described below. The interior of the nut 82 also has an elongated cylindrical cavity 90 within which a compression spring 92 is mounted which surrounds control rod 88 and normally urges the valve spool 86 against a valve seat 94, which is at the upper end of the intermediate portion of the cylindrical air port 44, for purposes of preventing passage of air through the compound valve unit 32 until such passage is desired, as when a dental handpiece is removed from the support 36 for operation upon a patient.

The interior of the molded compound valve body 32 contains a fluid passage 96, which extends transversely to the axes of, but communicates commonly with, the inner ends of all three cylindrical ports 44, 46 and 48 by means of lateral passages 98 and 100 respectively extending inwardly from the inner ends of the cylindrical ports 46 and 48, while the portion of cylindrical port 44 within which the spool 86 is disposed also communicates with the innermost end of the transverse fluid passage 96, as clearly shown in FIG. 8. For purposes of molding the passage 96 within the compound valve body 32, the outer end of the passage 96 is provided with threads to receive a plug 102 fixedly positioned therein and in view thereof, it will be seen that the entire compound valve body of the unit 32 may be molded in finished condition, including all threads therein, by injection molding and the employment of suitable threaded plugs in the mold or die within which the body is formed. Similarly, the body is provided with a plurality of transverse holes 104 through which screws or bolts may be inserted for attachment of the valve body to the lower surface of frame member 18, as clearly illustrated in FIG. 1. Further characteristics and purposes of the various elements mounted within the compound valve body 32 are set forth hereinafter.

HANDPIECE SUPPORT

Referring to FIG. 1, and particularly to FIGS. 2-6, attention is directed to the details of the support 36 for the handpiece 76, said support including a bracket 34, the latter preferably being formed from metal while the support 36 per se perferably is formed by injection molding from a suitable synthetic resin or plastics. The handpiece 76 has an air and water supply compound conduit 106 connected thereto. The support 36 is shell-like, as is best shown in certain of FIGS. 3-6 and a substantially horizontal upper portion 108, as well as the front face 110 thereof, is provided with an inlet slot 112 through which the conduit 106 of the handpiece 76 may pass in order that the lower end of the handpiece 76 may be disposed in the substantially cylindrical socket or seat 114 formed at the inner end of the slot 112 as best shown in FIGS. 2 and 3. The opposite sides 116 and 118 of the shell-like support 36 are pivotally connected respectively to parallel flanges 120 respectively at opposite sides of the horizontal portion of bracket 34 which abuts the undersurface of the sheet-like frame member 18. The purpose of the pivotal connection of the holder 36 to the bracket 34 is to permit the handpiece 76, for example, to be disposed selectively either in the vertical, rest position, as shown in full lines in FIG. 1, or in a forwardly inclined position as shown in phantom in FIG. 1; the arc of movement being relatively limited and preferably of the order of not greatly more than 45°, as can be visualized from FIGS. 1 and 6. To secure the desired adjustment, one of the flanges 120 is provided with an arcuate slot 122 through which a short bolt 124 extends through a depending gear 126 provided on side 116 of the support 36, for threaded engagement with a nut 128, see FIGS. 3 and 4, which is disposed against a washer bearing upon the adjacent flange 120 of bracket 34. Preferably, the bolt 124 is only lightly tightened so as to permit relative movement between the support and bracket by the application of limited force upon the support 36.

The bracket 34 and support 36 are mounted upon the frame member 18 forwardly of the compound valve unit 32 and in axial alignment with the control rod 88 thereof, as well as being adjacent the lower edge of the upstanding panel 20, as best shown in FIG. 1. One essential purpose of such arrangement is to provide a lockout for the air control valve from which the control rod 88 extends forwardly. When the handpiece 76 is disposed within the socket or seat 114, a pivoted control member 130 is disposed, at least at its lower end, within the socket or seat 114 and thereby readily is engageable by the lower end of the handpiece 76 when disposed within the seat or socket 114, especially as shown in phantom in FIG. 4. However, when the handpiece 76 is removed from the seat or socket 114 and air pressure is introduced to the compound valve unit 32 by virtue of depressing a single treadle 132 of a foot control 134, shown diagrammatically in FIG. 10, which essentially is a valve in the main line of the air supply, air pressure is introduced through inlet conduit 78 and projects the valve spool 86 forwardly, together with moving the control rod 88 forwardly, to the extended position thereof shown, for example, in FIGS. 5 and 6, whereupon air pressure is delivered to the handpiece for operation of the rotor thereof.

In customary dental operations, it is normal for the dental burs carried by the head of a dental handpiece to be replaced in order that burs of different shapes and capabilities may be mounted in the handpiece for operation in the oral cavity of a patient. In order to exchange one bur for another, it is essential to remove the handpiece from its seat in the console but to do this without suitable provisions being made for deactivating the supply of air to the handpiece, makes such exchange of a dental bur impossible. Accordingly, the present invention is provided with a suitable lockout mechanism, as follows:

LOCKOUT MECHANISM

The lockout mechanism of the present invention primarily comprises a manually-operable lever 136 including a radial member projecting from a semi-circular body 138, which is supported upon a transverse pin 140 supported primarily by one sidewall 116 of the shell-like support 36 and a parallel wall 142, see FIG. 3, provided on a sub-frame 144, fixed within the interior of the shell-like support 36, the lower surface of which is shown in FIG. 3.

the body 138 of the lever 136 is provided with a lateral projection 146 which engages a leg 148 which extends downwardly and at right angles to a horizontal pivoted portion 50 upon which one end of the pivoted control member 130 is fixed for support in actuation thereof by the leg 148 when engaged by the lateral projection 146 on the semi-circular body 138 of the manual lever 136 when in one position identified as the operative position. As best shown in FIG. 5, the leg 148 moves between the inoperative position shown in dotted lines in said figure and the operative position shown in phantom in said figure.

As viewed particularly in FIG. 4, it will be seen that one side of the body 138 of the lever 136 is provided with an additional block-like lateral projection 152, and as seen at the left-hand end of said projection in FIG. 4, there is a pair of angularly-related faces against which a leaf spring 154 is arranged to be disposed, the spring engaging one face when the lever 136 is in operative position and the opposite face, when it is in the inoperative position respectively to control the position of said lever and the semi-circular body 138 thereon. The spring 154 is L-shaped, as seen in FIG. 4, and the other leg 156 thereof is fixed to the bottom surface of the sub-frame 144 as shown in FIG. 3.

From the foregoing, it will be seen that when the radial lever 136 is in the phantom position thereof shown in FIG. 5, the lateral projection 146 will engage the leg 148 of the pivoted portion 150 of the right-angled wire-like member to the portion 150 of which the control member 130 is fixed and thereby will maintain the control member 130 against the outer end of control rod 88 on valve spool 86 of the air discharge port 64 and maintain said spool in closed position to prevent any transmission of air through the compound valve unit 32, whereby the handpiece may be removed readily from the seat or socket 114 in support unit 36, such as for the changing of a bur or otherwise, and the rotor of the handpiece will be rendered inoperative for purposes of such bur exchange, etc. Following such an exchange, if it is desired to immediately use the handpiece, the manual lockout lever 136 may be moved from the phantom position shown in FIG. 5 to the full line position shown therein, whereupon if the foot control treadle is depressed to deliver air to the compound valve unit 32, the control rod 88 of the latter will be projected to the extended position, such as shown in FIGS. 5 and 6, and thereby initiate the delivery of air to the handpiece for operation thereof. As otherwise explained, when the handpiece is disposed within the seat or socket 114, when the support 36 is either in vertical or inclined position, the handpiece will hold the control rod 88 in inoperative position.

It also will be seen further from the foregoing that the bracket 34 and support 36 for each handpiece in the console is mounted directly forwardly of the compound valve unit 32 for each of said handpieces, whereby when it is necessary to service said valves, on occasion, said bracket and support block ready access, particularly to the forward ends of said valve units. Accordingly, to obviate this difficulty and to render access to the valve units without interference from such brackets and supports, it will be seen particularly from FIG. 3, which is a bottom plan view of the frame member 18 to which the bracket 34 is secured, that a pair of screws 158 and 160 are threaded into the flat frame member 18 and respectively are received in complementary notches 162 and 164 formed in the rear edge portions of the bracket 34. Merely by slightly loosening said screws, the bracket 34 and the support 36 carried thereby easily are removed from obstructing the valve unit 32, whereupon it readily may be engaged, and if necessary, the bolts or screws which extend through holes 104 of the valve body likewise may be removed, and the flexible supply hoses 78 and 80 will permit the valve unit to be held in the hand of a serviceman or otherwise for suitable attention. Following such servicing of the valve, the same may be quickly restored to operative position and, upon tightening the screws 158 and 160, the bracket and support are restored to operative position.

FLUID DISTRIBUTION CIRCUIT

FIG. 10 comprises a schematic diagram of the fluid distribution circuit included in the present invention, particularly with respect to cold and warm water supply to the various handpieces and operating air under pressure for said handpieces. The foot control unit referred to hereinabove is illustrated within a square outline 134, which encloses the single foot treadle 132, and a chip air control 166. Air under pressure is introduced at a predetermined pressure, such as possibly as high as 80 psi through line 168, shown in FIG. 10. The main part of this air is delivered to the foot control unit 134 which, when opened by depressing the peddle 132, introduces air pressure to line 170, which includes branch lines 172, 174 and 176 respectively to dental handpieces 76, identified as handpieces Nos. 1, 2, and 3 in FIG. 10.

The warm water supply is introduced by line 178 which has branch lines 180, 182 and 184 leading therefrom respectively to the three handpieces and water will be delivered as desired to each handpiece if the toggle valve 28 therefor is open. Air from the branch lines 172, 174, and 176 also respectively is directed to the elongated cylindrical air port 44 in which spool valve 86 is mounted for operation by the pressure air when it is to be delivered to a handpiece. Regulation of the amount of such pressure air to the handpiece is controlled by the needle valve 62 in the compound valve unit 32 for each handpiece.

The water control valve 54 in each compound valve unit 32 also is arranged to be opened when the slidable piston 50 in each of the cylindrical air ports 48 is activated by air through the transverse fluid passage 96 in each of the compound valve units 32 as indicated by the dotted lines in the diagrammatically illustrated valve units in FIG. 10.

For purposes of rendering the air distribution circuit responsive to only a single pressure gage 26, regardless of the number of handpieces 76 and compound valve units 32 connected in said circuit, it will be seen that after the air is delivered by a line 170 to each valve unit 32, the air discharging from port 64 of the valve unit for handpiece No. 1, will pass along first air gage line 186 to one end of a first shuttle valve 188. This shutter valve is of conventional type and includes a pair of seats between which a single valve member 190 shuttles. In FIG. 10, the valve member 190 is shown in the upper seat but the air pressure delivered from conduit 186 will move it to the lower seat and correspondingly cause the air in line 186 to be registered in the gage 26. The opposite end of shuttle valve 188 communicates midway between the pair of seats in second shuttle valve 192 and in which a valve member 194 is shown disposed in the left-hand seat of shuttle valve 192 and drive air for handpiece No. 1 is delivered from branch air line 196, which receives air from line 186.

Drive air from valve unit 32 for handpiece No. 2 passes through second air gage line 198 which includes branch air line 200 that communicates with handpiece No. 2. However, line 198 continues for connection to the left-hand end of second shuttle valve 192 and when said handpiece No. 2 is operating, the valve member 194 of shuttle valve 192 will be moved to the right-hand seat and thereby permit said air to be discharged from air line 202, between the two shuttle valves, to the lower end of first shuttle valve 198, which then is opened, and from there to pressure gage 26.

Drive air for handpiece No. 3 receives the same through air line 204, which discharges to said handpiece No. 3, and a branch air line 206 leads from the line 204 to the right-hand seat of second shuttle valve 192, thereby moving the valve member 194, if necessary, to the left-hand seat as shown in FIG. 10, thereby clearing the shuttle valve for air passed through line 202 in a manner to seat the valve member 190 in the upper seat, thereby causing the air to be registered by gage 206. Accordingly, it will be seen from the foregoing that only a single gage 26 need be included in each console in which a plurality of handpieces are mounted for individual operation at any selected time. Similarly, in addition to drive air being delivered to each handpiece, water also is delivered thereto when the toggle valve 28 associated with each compound valve unit 32 is opened manually by actuating the handle 30 which is readily accessible on the front panel 20 of the console as clearly shown in FIG. 1.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A fluid control valve system for a dental handpiece requiring air pressure and a supply of water incident to operation thereof, said system including:
   (a) a compound valve body having
   (b) an air inlet port at one end of said body provided with a valve seat,
   (c) a valve spool in axial alignment with said port and having a control rod projecting beyond said air inlet port,
   (d) spring means normally urging said valve spool against said seat in said body,
   (e) an adjustable needle valve in the same end of said body as said air inlet port,
   (f) a water inlet port in the same end of said body as said air inlet port and needle valve and spaced transversely therefrom,
   (g) fluid passage means within said body extending between said air and water inlet ports and said needle valve,
   (h) a water control valve having a movable valve member within said body and communicating with said water inlet port,
   (i) a valve actuating piston within said body axially aligned with said movable valve member of said water control valve and said fluid passage means communicating with one face of said piston and operable by air pressure to engage said piston with said movable valve member,
   (j) said body also having a water discharge port in communication with said water control valve to deliver water to a dental handpiece when connected to said compound valve and an air discharge port in communication with said needle valve to deliver driving air to a dental handpiece when connected to said compound valve, and
   (k) a foot control valve connectable to a source of air under pressure and having a discharge port connected by a conduit to said air inlet port of said body, said valve having only a single foot pedal to actuate the same for delivery of air to said compound valve body.

2. The valve system according to claim 1 further including a manually operable water control valve in a water supply conduit leading from said water discharge port of said compound valve body and extending to a dental handpiece when connected to said conduit, thereby to prevent the passage of water to a handpiece when said manual valve is closed but permit such delivery to a handpiece when said valve is open and air pressure has moved said piston against said movable valve member of said water control valve in said compound valve body.

3. The valve system according to claim 1 further characterized by said compound valve body having three parallel elongated cylindrical ports in side-by-side relation, each extending inwardly from one end of said valve body to provide a compact arrangement and respectively comprising said water inlet port, a port to receive the adjustable valve member of said needle valve, and said air inlet port.

4. The valve system according to claim 3 in which the axes of said cylindrical ports are substantially within a common plane and said fluid passage means within said body also being within said plane and comprising a straight bore disposed transversely to the axes of said ports and said body further having branch passages extending from the inner ends of said cylindrical ports and intersecting said bore.

5. The valve system according to claim 1 in combination with a support for a dental handpiece comprising a bracket attachable to a fixed member of a dental console, a receptacle having a seat arranged to receive a dental handpiece, means pivotally connecting said receptacle to said bracket, adjustable position-maintaining means operable between said receptacle and bracket and adapted to permit relative pivotal movement therebetween through a predetermined arc and also including means to releasably fix said receptacle and bracket in a desired position relative to each other.

6. The valve system according to claim 1 further including a stationary frame member in a dental console provided with an outer edge, a support for a dental handpiece including a bracket and a receptacle having a seat to receive a dental handpiece, means affixing said bracket to said frame member adjacent said outer edge thereof, additional means affixing said compound valve body to said frame member rearwardly of said outer edge thereof and with said control rod of said compound valve body in alignment with and extending toward said bracket, and said receptacle including a control member engageable by a handpiece when supported by said receptacle and operable to engage the outer end of said control rod and maintain the same in position to prevent the inlet of air to said fluid passage means in said compound valve body, whereby said handpiece is rendered immobile.

7. The valve system according to claim 6 further including a lockout for said control member comprising a movable member supported adjacent said control member of said receptacle for movement between engaging and disengaging positions relative to said control member and interengaging the said control member when in said engaging position to maintain said control member against said control rod and thereby permit removal of said handpiece from said receptacle without initiation of operation of said handpiece, such as to permit changing a bar or otherwise.

8. The valve system according to claim 7 in which said movable member comprises a lever pivotally supported adjacent said control member and movable between operative and inoperative positions, said lever having means engaging said control member when in said operative position to secure the same releasably in holding engagement against said control rod, and resilient means engageable with said lever and operable to releasably hold the same selectively in said operative and inoperative positions.

9. The valve system according to claim 6 in which said stationary frame member is plate-like and said bracket has a relatively flat portion extending away from said receptacle for a handpiece and adapted to engage said plate-like frame member adjacent the outer edge thereof, and said flat portion of said bracket having means to receive attaching means of a quickly operable type to secure the same to said frame member thereby to permit removal of said bracket and receptacle from said frame member and provide ready access to said compound valve body and the fluid control elements supported therein and thereby.

10. The valve system according to claim 1 further including a manually operable water control valve in a water supply conduit leading from said water discharge port of said compound valve body and extending to a dental handpiece when connected to said conduit, in combination with a dental console housing enclosing said valve system and water control valve and said housing including an upstanding front panel in the upper portion thereof, said water control valve being mounted upon said panel for ready accessibility and said support for a dental handpiece being supported adjacent the lower end of said panel and forwardly thereof for ready access of a handpiece when supported thereby.

11. The valve system according to claim 1 in combination with a dental console housing enclosing said valve system and including an upstanding front panel in the upper portion thereof and also including a frame member extending transversely to the lower edge of said front panel and rearwardly therefrom, a support for a handpiece comprising a bracket secured to said frame member adjacent the forward edge thereof, a receptacle pivotally connected to said bracket for movement about a horizontal axis and positioned forwardly of said front panel for reception of a dental handpiece and operable relative to said bracket to fix said receptacle selectively as desired between a vertical position and a forwardly inclined position, and the outer end of said control rod on said valve spool projecting forwardly into said receptacle to an operative position when a handpiece is removed therefrom but depressed rearwardly to an inoperative position for said valve system when a handpiece is positioned in said receptacle.

12. The valve system according to claim 11 further including lockout mechanism operable relative to said receptacle and including a lever movable manually between operative and inoperative positions thereof, said mechanism also having means operable to engage said outer end of said control rod to render the valve system controlled thereby inoperable when a handpiece is removed from said receptacle.

13. The valve system according to claim 1 in combination with a vertical dental console housing and at least one additional valve system in side-by-side relation in the upper portion of said housing, said console having an upstanding panel in the front of said upper portion of said housing and each valve system having associated with said panel a support for a dental handpiece to which operating air and/or water is delivered and controlled by said valve systems respectively for said handpieces, an air pressure gage mounted upon said panel and connected by an air conduit system commonly to all of said valve systems, and a first shuttle valve connected in conduits of said conduit system between a first conduit to a first valve system for a first handpiece and said pressure gage and a second shuttle valve connected to one end of said first shuttle valve and within a second conduit between second and third valve systems for second and third handpieces.

14. The valve system according to claim 13 further including a foot control valve having a single actuator pedal connected to said first air conduit to said first valve system and thereby commonly furnish operating air to any selected handpiece and the valve system therefor.

15. A compact fluid control valve unit for furnishing air and water to a dental handpiece and comprising in combination, a compound valve body provided with a plurality of parallel elongated cylindrical inlet ports in side-by-side relationship extending into said body from one end thereof, a fluid passage extending within said body transversely to the axes of said inlet ports and commonly communicating with the inner ends of said ports, one of said ports having means on the outer end thereof for connection with a source of air, a second of said ports having means on the outer end for connection with a source of water under pressure, a valve spool yieldably maintained against the inner end of said one of said ports and normally closing said inner end of said port from communication with said transverse fluid passage, a needle valve member threaded within a third one of said plurality of ports and having a valve member movable toward and from a valve seat at the inner end of said port and adjacent an air discharge port in said body, a piston mounted within the inner end of said second of said plurality of ports which is connected to a source of water and said transverse fluid passage communicating with the inner end of said piston, and a movable water inlet control valve member mounted within said second port and movable to open position by said piston when moved against said valve member by air pressure from said transverse passage and said second port also having a water discharge port exiting therefrom through which water discharges when said water inlet valve member is open, whereby air pressure delivered to said air inlet port serves to move said valve plug away from the inner end of said air inlet port for passage of air to said transverse fluid passage and respectively to said needle valve and piston to move said water control valve member to open position for discharge of air and water to a handpiece.

16. The control valve unit according to claim 15 further characterized by said compound valve body being injection molded from synthetic resin material of firm nature and the exterior of said body comprising three generally tubular configurations in integral side-by-side relationship with said plurality of ports being formed respectively axially in said configurations, said outer ends of said ports being threaded interiorly for connection of conduit fittings thereto and the intermediate port receiving a threaded needle valve member, the opposite end of said one of said plurality of elongated ports also being threaded to receive a guide tube and said valve spool in said one port having an elongated control rod slidable in said guide tube and extending beyond the outer end of said tube, and the interior of said guide tube having clearance to receive a compression spring surrounding said control rod and urging the spool thereon against the inner end of said air inlet port.

17. The control valve unit according to claim 15 further characterized by said compound valve body being injection molded from synthetic resin material of firm nature and the exterior of said body comprising three generally tubular configurations in integral side-by-side relationship with said plurality of ports being formed respectively axially in said configurations, said elongated port containing said needle valve having an exterior boss projecting laterally from the wall of the tubular configuration of said port and said boss having a threaded outlet hole therein communicating with the interior of said port adjacent said valve seat therein and comprising said air outlet port and adapted to receive one end of a fitting for an air discharge tube, and said tubular configuration in which said elongated port which contains said piston is located also having a similar boss thereon provided with a threaded outlet hole comprising said water discharge port and adapted to receive one end of a fitting for a water discharge tube.

* * * * *